United States Patent [19]
Kurata

[11] 4,231,988
[45] Nov. 4, 1980

[54] ARTIFICIAL LUNG

[75] Inventor: Motoji Kurata, Hiroshima, Japan

[73] Assignee: Japan Medical Supply Co., Ltd., Hiroshima, Japan

[21] Appl. No.: 48,447

[22] Filed: Jun. 14, 1979

[30] Foreign Application Priority Data

Jun. 13, 1978 [JP] Japan .................................. 53/70328

[51] Int. Cl.³ ............................................. A61M 1/03
[52] U.S. Cl. ...................................... 422/47; 55/255; 55/256; 128/DIG. 3; 261/122; 261/124; 261/DIG. 28
[58] Field of Search ........................ 422/45, 46, 47, 48; 55/255, 256; 261/122, 124, DIG. 28; 128/DIG. 3; 210/522

[56] References Cited

U.S. PATENT DOCUMENTS

| | | | |
|---|---|---|---|
| 3,807,958 | 4/1974 | Brumfield et al. | 422/47 |
| 4,058,369 | 11/1977 | Bentley et al. | 422/47 |
| 4,160,801 | 7/1979 | Baddlato et al. | 422/46 |

OTHER PUBLICATIONS

"Clinical Evaluation of New Harvey H200 ... Oxygenator" P. Space et al., Jour. of Ther. and Card. Surgery, vol. 67, No. 2, 2/1974 p. 213.

"Bentley Spiraflow BOS-10 Disposable Oxygenator", Bentley Lab., Irvine, Calif. 1977.

Primary Examiner—Charles N. Hart
Assistant Examiner—David R. Sadowski
Attorney, Agent, or Firm—Armstrong, Nikaido, Marmelstein & Kubovcik

[57] ABSTRACT

An artificial lung having first and second oxygen blowing stages formed therein. The device comprises an outermost blood reservoir tube having top and bottom walls formed thereon, a plurality of oxygenation tubes disposed coaxially with the blood reservoir tube defining passages for blood therebetween, a first oxygen blowing stage formed under the oxygenation tubes for blowing oxygen gas into the blood introduced through an inlet for blood and a second or auxiliary oxygen blowing stage formed around the first oxygen blowing stage.

4 Claims, 3 Drawing Figures

ARTIFICIAL LUNG

BACKGROUND OF THE INVENTION

This invention relates to an oxygenator device used for surgery of chests and more particularly to an artificial lung.

There have theretofore been employed oxygenator devices of disk type, membrane type, sheet type and hard shell type. The sheet type and hard shell type artificial lungs are bubble type devices which have been widely used lately. Such conventional bubble type artificial lungs are disadvantageous in that they cannot provide a satisfactory oxygenation and tends to cause a problem regarding the oxygenation efficiency, and also at the time of extra-corporial circulation at high flow rates, the amount of oxygen at high flow rates of blood will increase with increases in the blood's extra-corporial circulation quantity as compared with those at low flow rates thus creating a remarkable decrease in oxygenation efficiency. Further, such devices are unsatisfactory as an artificial lung in that a proper ratio of mixing blood and oxygen cannot always be obtained and exceeding the proper mixing ratio will cause a hemolytic problem.

SUMMARY OF THE INVENTION

It is therefore an object of the present invention to provide an artificial lung which is capable of controlling pressures of $O_2$ and $CO_2$.

Another object of the present invention is to provide an artificial lung wherein the ratio of the amount of blood to that of oxygen can be kept constant throughout high and low flow rates of blood. A further object of the present invention is to provide an artificial lung which can enhance the oxygenation efficiency of blood by improving diffusion capability of the mixture of blood and oxygen.

In accordance with an aspect of the present invention, there is provided an artificial lung comprising a blood reservoir tube having top and bottom walls formed thereon; a first oxygenation tube disposed coaxially with said blood reservoir tube within the same, said first oxygenation tube terminating adjacent to but spaced from the top wall; a second oxygenation tube disposed coaxially with said blood reservoir tube between said first oxygenation tube and said blood reservoir tube, said second oxygenation tube being fixedly secured to the top wall and terminating adjacent to but spaced from the bottom wall; a third oxygenation tube disposed coaxially with said blood reservoir tube between said second oxygenation tube and said blood reservoir tube, said third oxygenation tube being fixedly secured to the bottom wall and terminating adjacent to but spaced from the top wall; an innermost wall structure defining a first oxygen chamber therein disposed under said first oxygenation tube; an intermediate wall structure connected to the lower end of said first oxygenation tube; an outer wall structure fixedly secured to the bottom wall of said blood reservoir tube, said intermediate wall structure and said outer wall structure being adapted to define a second oxygen chamber therebetween; an inlet for blood connected to the inside of said first oxygenation tube; an outlet for blood connected to the inside of said blood reservoir tube; and an inlet for oxygen connected to the first and the second oxygen chambers whereby oxygen is blown into blood through the first and the second oxygen chambers while blood is passing through said oxygenation tubes.

The above and other objects, features and advantages of the present invention will be readily apparent from the following description taken in conjunction with the accompanying drawings.

DESCRIPTION OF THE PREFERRED EMBODIMENT

The present invention will now be described by way of embodiment with reference to the accompanying drawings.

Figure 1:
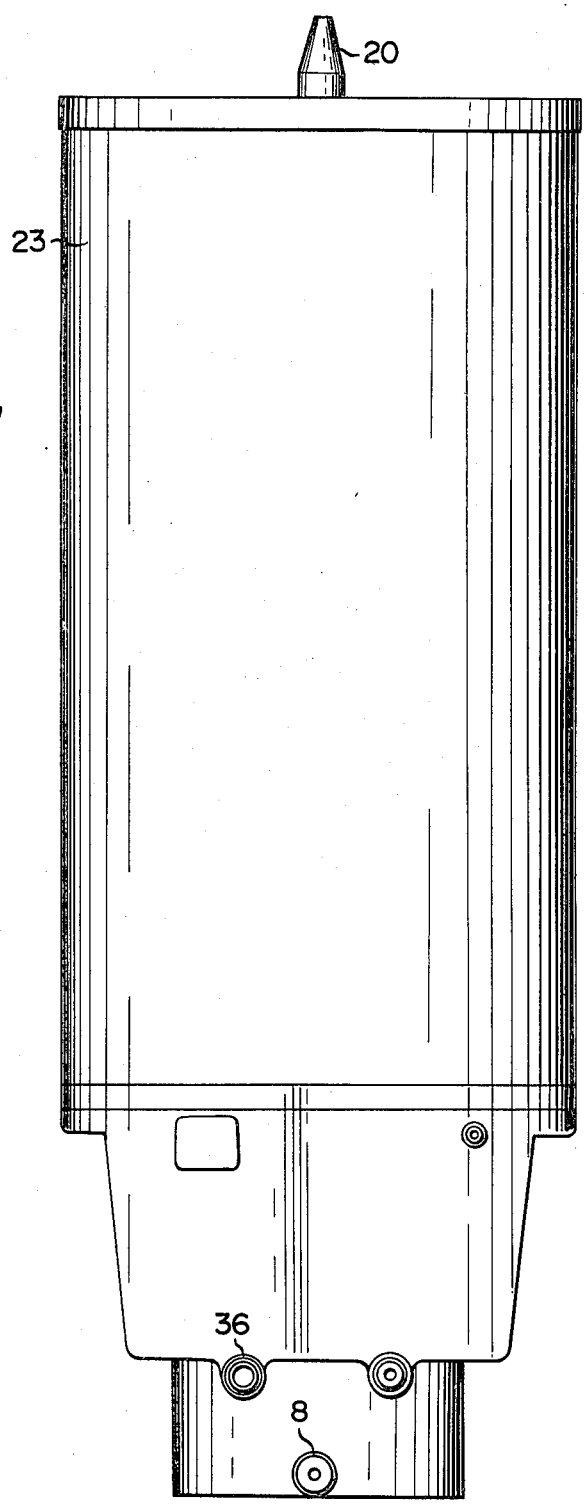
FIG. 1 is a front elevational view of an artificial lung according to the invention.
Figure 2:
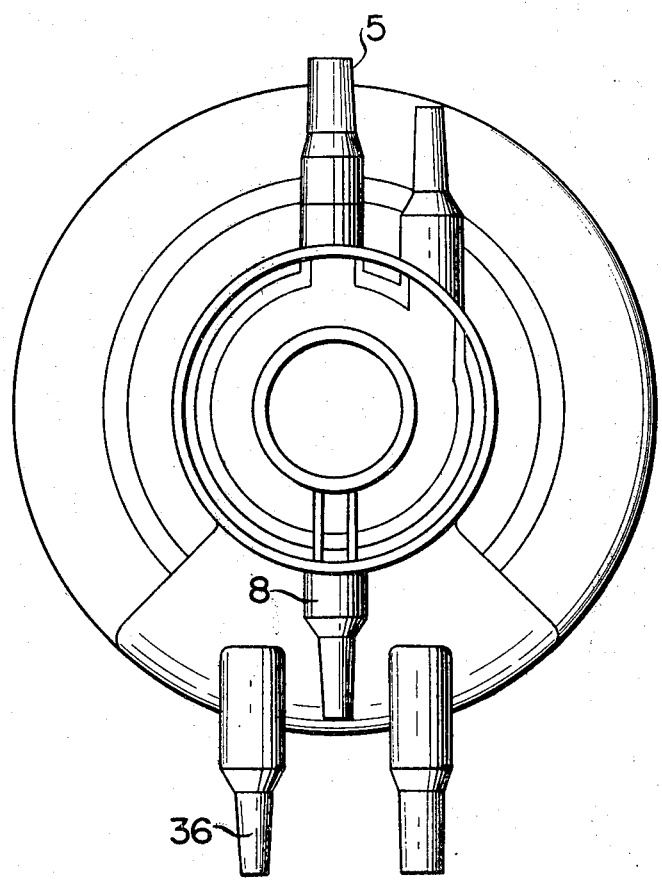
FIG. 2 is a bottom view thereof.
Figure 3:
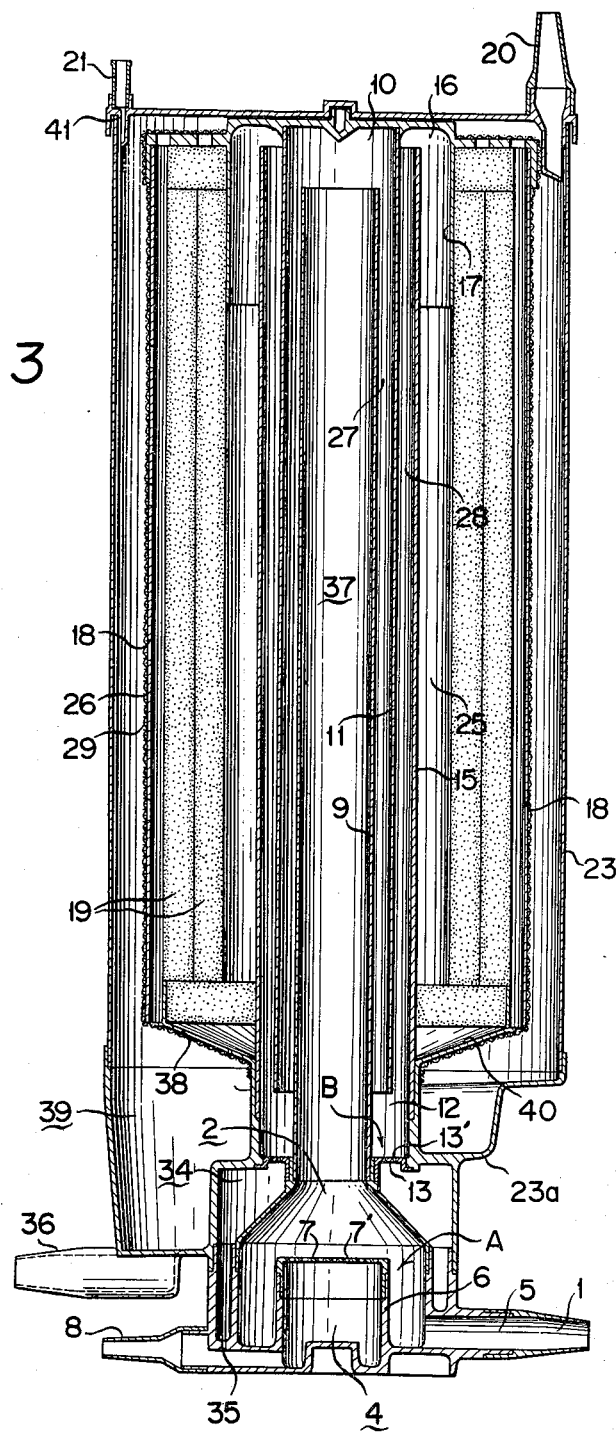
FIG. 3 is a longitudinal cross-sectional view thereof.

Referring to FIG. 3, reference numeral 23 denotes a blood reservoir tube in which are coaxially disposed a first oxygenation tube 9, a second oxygenation tube 11, a third oxygenation tube 15 and an air bubble eliminating tube 26.

The lower part of the third oxygenation tube 15 is fitted in a bottom member 23a of the blood reservoir tube 23.

Formed in the lower part of the above-mentioned first oxygenation tube 9 are a first mixing chamber 2 and an oxygen chamber 4 of a first oxygen injecting or blowing unit "A". An oxygen inlet port 8 is connected to the oxygen chamber 4, and the oxygen chamber 4 has at its upper part a first oxygen injecting plate 7 having a plurality of first oxygen injecting or blowing ports 7' formed therein and leading to the first mixing chamber 2.

Formed in the lower part of the first oxygenation tube 9 is an inlet 5 for venous blood. Both the inlet 5 for venous blood and the first oxygen injecting port 7' communicate with the first oxygenation tube 9. Formed between the lower part of the first oxygenation tube 9 and the bottom member 23a is a second oxygen injecting plate 13 of a second oxygen injecting or blowing unit "B". The second oxygen injecting plate 13 has a second oxygen injecting port 13'. A second oxygen chamber 34 defined under the second oxygen injecting plate 13 communicates through an orifice 35 with the oxygen inlet port 8. Formed within the first oxygenation tube 9 is a first passage 37 for blood. A second passage 27 is defined between the first oxygenation tube 9 and the second oxygenation tube 11, and a third passage 28 is formed between the second oxygenation tube 11 and the third oxygenation tube 15. Further, a fourth passage 25 is formed within the blood reservoir tube 23, and an oxygenated blood guiding tube 17 is located between the third oxygenation tube 15 and the bubble eliminating tube 26. A first oxygenated blood damping chamber 10 is defined in the boundary part of the inside of the first oxygenation tube 9 or the first passage 37 and the second passage 27. Formed in the boundary of the passages 27 and 28 is a second mixing chamber 12. Further, a second oxygenated blood damping chamber 16 is formed in the upper part of the third passage 28.

The aforementioned bubble eliminating tube 26 has a plurality of outlet ports 18 for blood formed in the periphery thereof, and also has a corrugated polyester cloth 29 adhered to the outer surface thereof. Mounted inside the air bubble eliminating tube 26 is a foamed urethane 19.

Fixedly secured to the lower end of the air bubble eliminating tube 26 is a funnel-shaped stationary disk 40, the lower end of which is fixedly secured to the bottom member 23a of the blood reservoir tube 23. The funnel-shaped stationary disk 40 has a plurality of openings 38 formed in the peripheral direction thereof and at predetermined space intervals.

A blood reservoir pocket 39 formed in the lower part of the blood reservoir tube 23 had an outlet port 36 for arterial blood.

In the drawing, reference numerals 20 and 21 denote priming ports, and 41 a gas outlet port.

The operation of the artificial lung according to the present invention will now be described.

The venous blood 1 taken out of the interior of a human body will flow through the inlet port 5 for venous blood and move upwards smoothly along the cylindrical passage of a blood diffusion wall 6. The upwardly moving venous blood 1 is mixed with the oxygen gas injected through the oxygen injecting ports 7' of the first oxygen injecting plate 7 within the first mixing chamber 2 located in the lowermost part of the first oxygenation chamber 9 and then move upwards inside the chamber 9. The blood which has mixed with oxygen gas will enter the second oxygenation tube 11 through the first oxygenated blood damping chamber 10. The reason for the provision of the damping chamber 10 is that since the direction of flow of the oxygenated blood is changed 180 degrees, it is desirable to change the direction of flow of blood from a condition where blood is stored in a predetermined space. When flowing into the second oxygenation tube 11, the direction of flow of the blood is changed so that the oxygenated blood can be diffused. The diffusion of the oxygenated blood is very important in gas exhange. Excellent diffusions can enhance a chance of contact of hemoglobin in the blood with oxygen gas. The oxygenated blood which has descended within the second oxygenation tube 11 is further mixed with the oxygen gas injected through the second oxygen injecting portion 13' of the second oxygen injecting plate 13 within the second mixing chamber 12, thereby enabling the hemoglobin which has not been brought yet into contact with oxygen gas to be exchanged with gas and increasing the oxygenation efficiency.

Where the total amount of injected oxygen gas is 1 to 2 liters, the ratio of the amount of the oxygen gas injected by the first oxygen injecting unit to that by the second oxygen injecting unit is 6:4.

Where the total amount of injected oxygen gas is 3 to 4 liters, the ratio of the amount of the oxygen gas injected by the first oxygen injecting unit to that by the second injecting unit is 7:3.

Where the total amount of injected oxygen gas is 5 to 6 liters, the ratio of the amount of the oxygen gas injected by the first oxygen injecting unit to that by the second injecting unit is 7.5:2.5.

Where the total amount of injected oxygen gas is more than 6 liters, the ratio of the amount of oxygen gas injected by the first oxygen injecting unit to that by the second oxygen injecting unit is 8:2.

The arrangement is made such that the ratio of the amount of the oxygen gas injected by the first oxygen injecting unit to that by the second oxygen injecting unit can be automatically controlled by increasing or decreasing the amount of injection of oxygen. The automatic control is determined by the orifice 35 which is connected to the second oxygen chamber 34. This orifice 35 has a diameter ranging from 0.4 mm to 1.0 mm. When the supply of oxygen gas or oxygenation is made to convert venous blood into arterial blood and where the gas exchange capability is high, the degree of oxygenation can be controlled by reducing the total amount of injection of oxygen gas. Usually, if the ratio of the flow rate of blood to the amount of injection of oxygen gas is 1:2, a proper gas exchange capability can be obtained. Further, in case a sign of peroxidation of blood is observed, the peroxidation can be prevented by adjusting the amount of the oxygen gas to be injected through the second oxygen injecting plate 13. The blood which has been mixed with oxygen gas for the second time within the second mixing chamber 12 will move upwards within the third oxygenation tube 15. At that time, in the like manner as in the case of the second oxygenation tube 11, a phenomenon will occur in which air bubbles move upwards along the interior wall of the oxygenation tube 15. In brief, air bubbles are converted into films so that blood layers can be produced in the clearances among the air bubbles. For this purpose, the clearance between the second oxygenation tube 11 and the third oxygenation tube 15 should desirably be 2 to 3 mm, and if the clearance is less than the above figure the speed of flow of the blood will increase thereby causing a problem on rupture or breakdown of blood-corpuscles. The oxygenated blood which has ascended within the third oxygenation tube 15 will enter the second oxygenated blood damping chamber 16 where its direction of flow is changed 180 degrees, and then is guided by the oxygenated blood guiding tube 17 into the air bubble eliminating chamber 25. Disposed inside the air bubble eliminating chamber 24 are urethane foams 19 the surface of which are applied with air bubble eliminating agent which serves to eliminate air bubbles in the blood passing therethrough. The blood which has become free from air bubbles will pass through the openings 18, 38 and the polyester cloth covering the whole surface of the air bubble eliminating tube 26 and then is stored in the blood reservoir tube 23. the polyester cloth 29 serves as a filter to remove foreign matters having a particle size of more than $\phi\mu$.

Defined in the lower part of the blood reservoir tube 23 is the pocket portion 39 in which blood of about 300 ml is stored.

The blood stored in the blood reservoir tube 23 will flow out through the blood outlet port 36 as arterial blood.

Further, when the oxygenated blood having descended through the second passage 27 into the third passage 28, the oxygenated blood is forcibly guided into the third passage 28 partially by the action of the oxygen gas injected through the second oxygen injecting plate 13 into the passage 28, thereby causing repeated changes of the direction of flow of blood at 180 degrees and enabling blood to flow smoothly within the oxygenation tubes.

As mentioned in detail hereinabove, the present invention comprises a first passage 37 in which venous blood is introduced, a first oxygen injecting unit "A" defined in the lower part of the first passage 37 to inject oxygen gas into venous blood, a second passage 27 communicating at the upper part thereof with the first passage 37, a third passage 28 communicating at the lower part thereof with the second passage 27, a second oxygen injecting unit "B" defined in the lower part of the third passage 28 to inject oxygen gas into blood, a fourth passage 25 communicating at the upper part thereof with the third passage 28 and having at the lower part thereof an outlet port for arterial blood, a second oxygen chamber 34 communicating with the second oxygen injecting unit "B", and an orifice 35 communicating the inlet side of the first oxygen injecting unit "A" with the second oxygen chamber 34. Therefore, the oxygenation efficiency can be controlled by installing the second oxygen injecting unit "B" and controlling variations in the amount of the oxygen gas to be injected by the second oxygen injecting unit "B". Further, a proper ratio can be maintained between the flow rate of blood and the amount of injection of oxygen gas without changing the ratio at high and low flow rates of blood. Still further, according to the present invention, the ratio of the flow rate of blood to the amount of injection of oxygen gas can be kept constant without requiring any inefficient operation to change the ratio and the hemolysis can be reduced, and the provision of the second and third passages enables oxygenation of blood to be made at a high efficiency. Further, when the blood flows from the first passage into the second passage, the direction of flow of blood is changed 180 degrees, and also when the blood flows from the second passage into the third passage, the blood will again change its direction of flow 180 degrees so that blood can be diffused enough to contact with oxygen gas. The provision of the second oxygen injecting unit "B" in the lower part of the third passage prevents possible generation of inefficient turbulence and breakdown of blood corpuscles, thereby enabling efficient blood diffusion to be achieved.

The provision of the second oxygen injecting unit "B" enables the control of pressures of $O_2$ and $CO_2$ which has been difficult to be made in the past, and reduces the amount of blood to be charged into the artificial lung, and also keeps constant the ratio of the flow rate of blood to the amount of injection of oxygen gas throughout high and low flow rates of blood. Further, when blood is peroxidized, the pressure of oxygen gas can be controlled by adjusting the amount of oxygen gas to be injected by the second oxygen injecting unit "B".

When the flow rate of blood is low, the ratio of the amount of oxygen gas to be injected by the first oxygen injecting unit to that by the second oxygen injecting unit is 6:4 whilst when the maximum flow rate of blood is about 6 liters, the said ratio will become 8:2. In brief, where blood is kept contact with oxygen gas for a long time, the amount of injection of oxygen gas is reduced, and where the time for contacting blood with oxygen gas is short, the amount of injection of oxygen gas is increased thereby enabling a proper oxygenation efficiency to be maintained. For this purpose, a method of reducing the amount of the oxygen gas to be brought into contact with blood and reducing the effect of oxygen gas to blood is employed. Further, when the mixture of blood and oxygen gas flows from the first oxygenation tube into the second oxygenation tube, air bubbles in the oxygen gas tends to move upwards due to their buoyancy so as to cause a proper turbulence in the flow of the mixture of blood and oxygen gas thereby allowing blood and oxygen gas to be kept into contact effectively.

Thus, unlike the conventional artificial lung, according to the present invention, depending on changes in the amount of injection of oxygen gas due to changes in the flow rate of blood, the amount of oxygen gas to be injected by the first oxygen injecting unit "A" and the second oxygen injecting unit "B", respectively, can be automatically controlled, and also changing the direction of flow of the mixture of blood and oxygen gas 180 degrees will produce buoyant air bubbles in the oxygen gas, the direction of flow of which is reverse to that of blood thereby enabling the effective area of contact between the blood and oxygen gas to be increased substantially.

It should be understood that the present invention is not limited to the aforementioned embodiment only, but may be modified without departing from the scope of the appended claims.

What is claimed is:

1. An artificial lung comprising:
   a blood reservoir tube having top and bottom walls formed thereon;
   a first impervious oxygenation tube disposed coaxially with said blood reservoir tube within the same, said first oxygenation tube terminating adjacent to but spaced from the top wall;
   a second impervious oxygenation tube disposed coaxially with said blood reservoir tube between said first oxygenation tube and said blood reservoir tube defining a first annular space, said second oxygenation tube being fixedly secured to the top wall and terminating adjacent to but spaced from the bottom wall;
   a third impervious oxygenation tube disposed coaxially with said blood reservoir tube between said second oxygenation tube and said blood reservoir tube defining second and third annular spaces, said third oxygenation tube being fixedly secured to the bottom wall and terminating adjacent to but spaced from the top wall;
   an innermost wall structure defining a first oxygen chamber therein open to and disposed under said first oxygenation tube;
   an intermediate wall structure connected to the lower end of said first oxygenation tube;
   an outer wall structure fixedly secured to the bottom wall of said blood reservoir tube, said intermediate wall structure and said outer wall structure defining a second oxygen chamber therebetween open to and disposed below said third oxygenation tube;
   a blood inlet connected to the inside of said first oxygenation tube;
   a blood outlet connected to the annular space between said third oxygenation tube and said blood reservoir tube; and
   an oxygen gas inlet connected to the first and the second oxygen chambers whereby oxygen is blown into blood through the first and the second oxygen chambers while blood is passing through the annular spaces between said oxygenation tubes.

2. An artificial lung as recited in claim 1 further comprising an air bubble eliminating tube disposed coaxially with said blood reservoir tube between said third oxygenation tube and said blood reservoir tube, and defoaming means disposed between said third oxygenation tube and said air bubble eliminating tube.

3. An artificial lung as recited in claim 2 wherein said air bubble eliminating tube has a plurality of holes formed in the periphery thereof and wherein a corrugated porous film is adhered to the outside surface of said air bubble eliminating tube.

4. An artificial lung as recited in claim 1 wherein said second oxygen chamber is connected to said oxygen gas inlet through orifice means.

* * * * *